US011166710B2

(12) United States Patent
Radl et al.

(10) Patent No.: US 11,166,710 B2
(45) Date of Patent: Nov. 9, 2021

(54) INTRA-ABDOMINAL LIVER RETRACTION DEVICE AND METHOD OF USE

(71) Applicant: Boehringer Technologies, LP, Phoenixville, PA (US)

(72) Inventors: Christopher L. Radl, Malvern, PA (US); Steven C. Moulden, West Chester, PA (US); William Charles Dackis, Philadelphia, PA (US); Malena Giselle Farber, Northport, NY (US)

(73) Assignee: Boehringer Technologies, LP, Phoenixville, PA (US)

( * ) Notice: Subject to any disclaimer, the term of this patent is extended or adjusted under 35 U.S.C. 154(b) by 213 days.

(21) Appl. No.: 16/736,187

(22) Filed: Jan. 7, 2020

(65) Prior Publication Data
US 2020/0297335 A1 Sep. 24, 2020

Related U.S. Application Data

(60) Provisional application No. 62/820,368, filed on Mar. 19, 2019.

(51) Int. Cl.
*A61B 17/02* (2006.01)
*A61B 17/34* (2006.01)

(52) U.S. Cl.
CPC ...... *A61B 17/0281* (2013.01); *A61B 17/0218* (2013.01); *A61B 17/34* (2013.01); *A61B 2017/0225* (2013.01)

(58) Field of Classification Search
CPC . A61B 17/02; A61B 17/0218; A61B 17/0281; A61B 2017/0212; A61B 2017/0225; A61B 17/34

USPC .......................................... 600/37, 204, 210
See application file for complete search history.

(56) References Cited

U.S. PATENT DOCUMENTS

| 8,449,461 | B2 | 5/2013 | Kim et al. |
| 9,974,532 | B2 | 5/2018 | Baas et al. |
| 2008/0081945 | A1 | 4/2008 | Toso et al. |
| 2009/0137877 | A1 | 5/2009 | Minnelli et al. |
| 2009/0171143 | A1 | 7/2009 | Chu et al. |
| 2009/0221868 | A1 | 9/2009 | Evans |
| 2018/0263613 | A1* | 9/2018 | Wik .................... A61B 17/0218 |

OTHER PUBLICATIONS

Newly Developed Liver-Retraction Method For Laparoscopic Gastric Surgery Using A Silicone Disc: The ϕ-Shaped Technique, by Hiroshi Saeki, MD, et al. appearing on pp. e43-e46 of Journal of American College of Surgeons © 2013.

* cited by examiner

*Primary Examiner* — Eduardo C Robert
*Assistant Examiner* — Christina Negrellirodriguez
(74) *Attorney, Agent, or Firm* — Caesar Rivise PC

(57) ABSTRACT

An intra-abdominal liver retraction device and methods of use. The device includes a flexible sling, an anchor and a filament. The sling has a base edge and a pair of side edges tapering toward a leading edge. The sling also includes a stiffener extending across it adjacent the base edge to enable it to be gathered and inserted through a port into the abdomen, whereupon it can be opened. The anchor is configured to be releasably secured to the diaphragm with the base edge adjacent the diaphragm so that the liver can be disposed on the sling. The filament is connected to the sling adjacent the leading edge and configured to be drawn through an aperture in the abdominal wall to lift the sling with the liver thereon upwards.

20 Claims, 4 Drawing Sheets

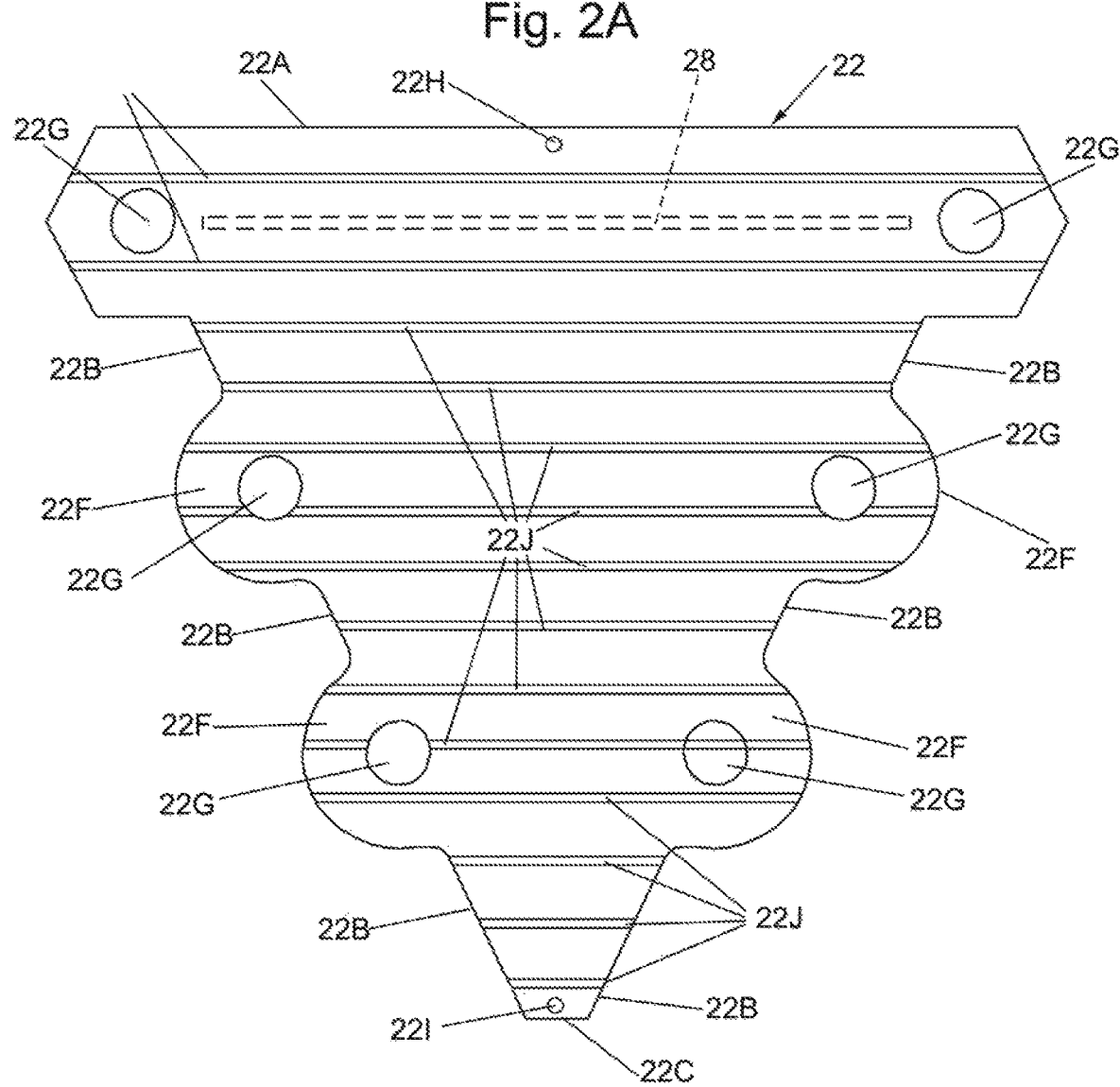
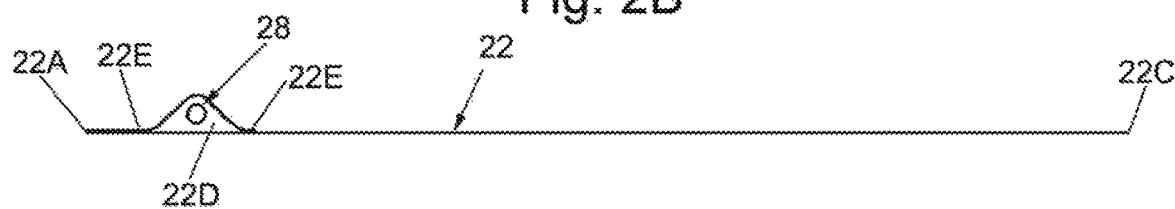

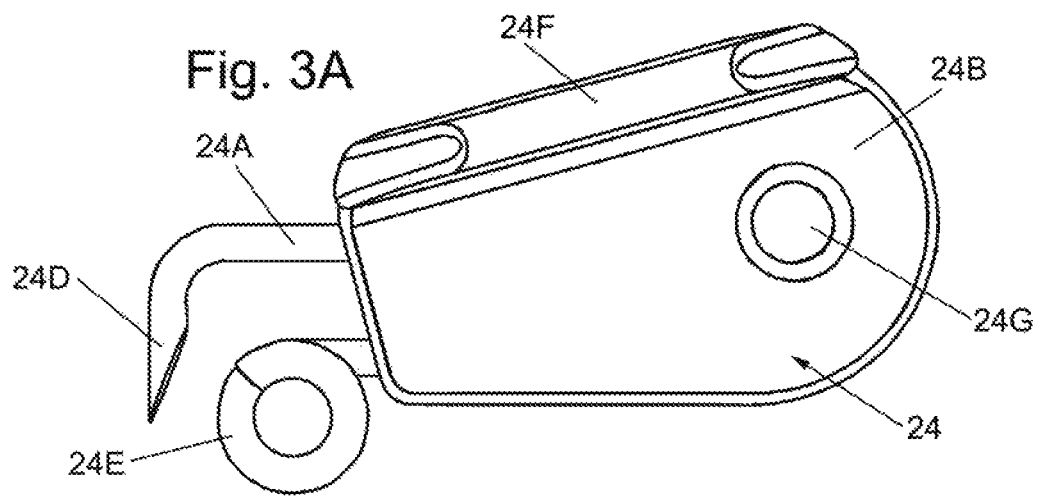
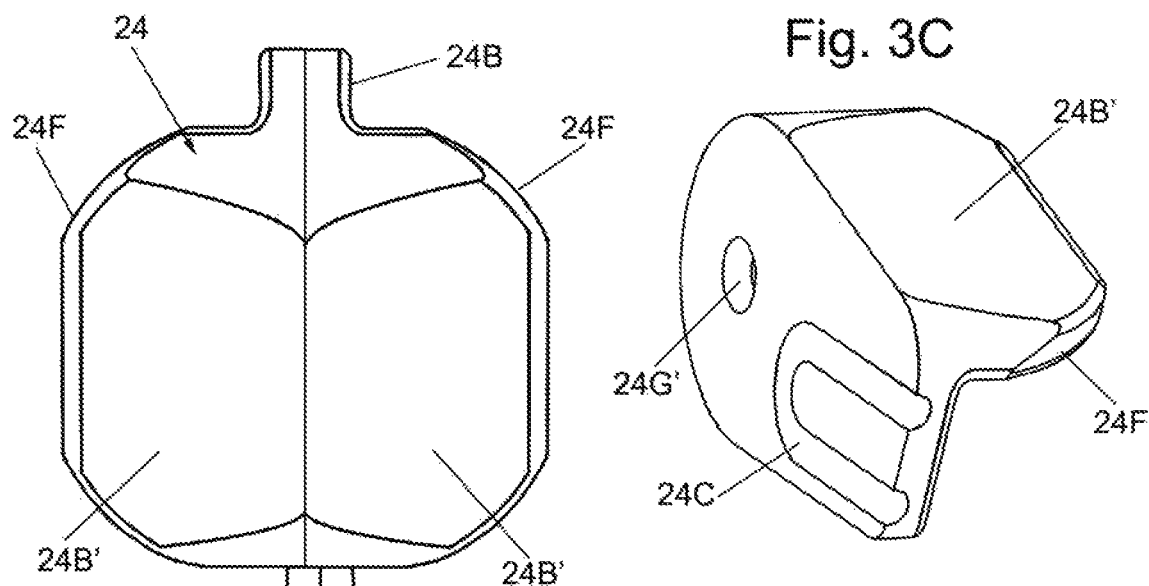
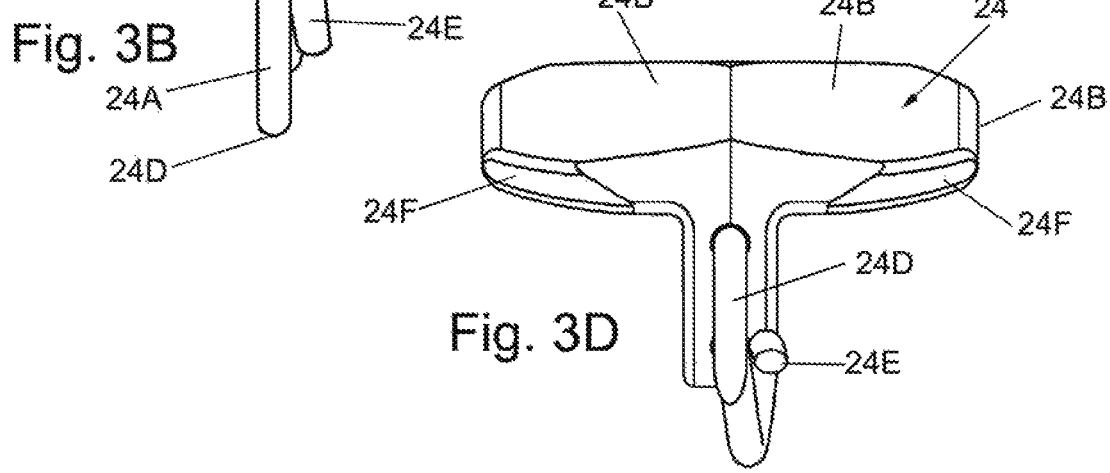

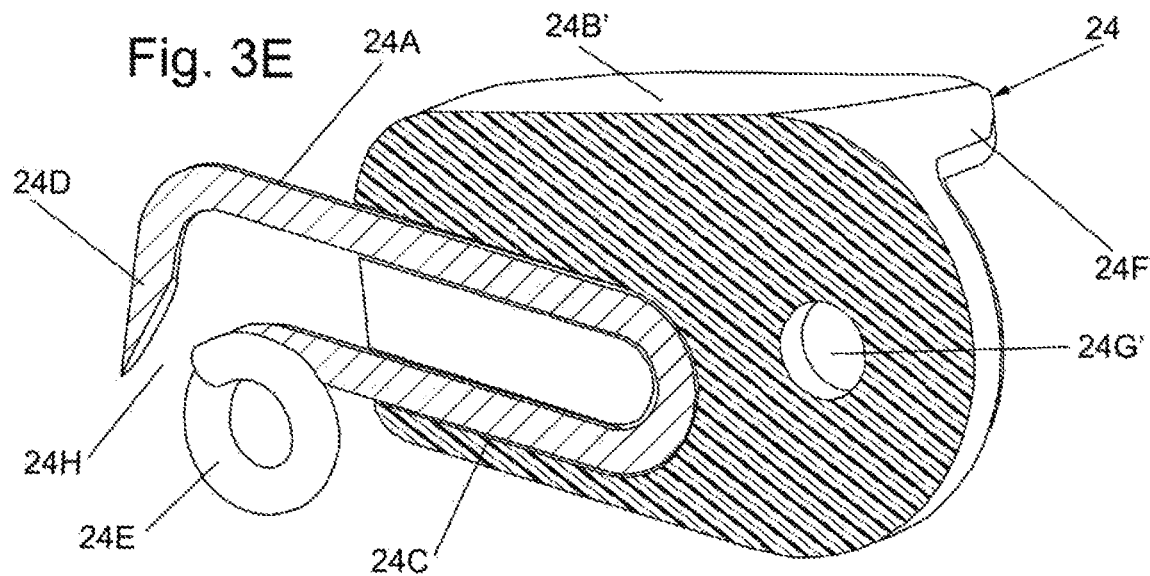
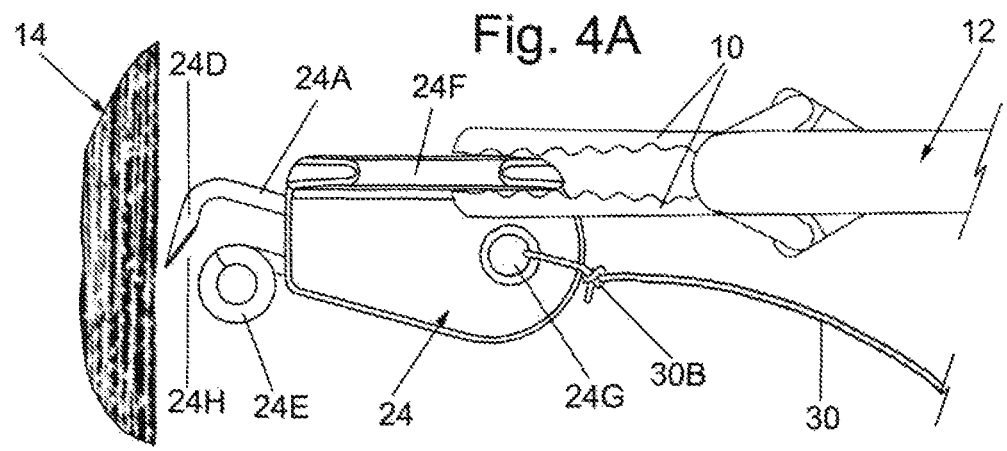
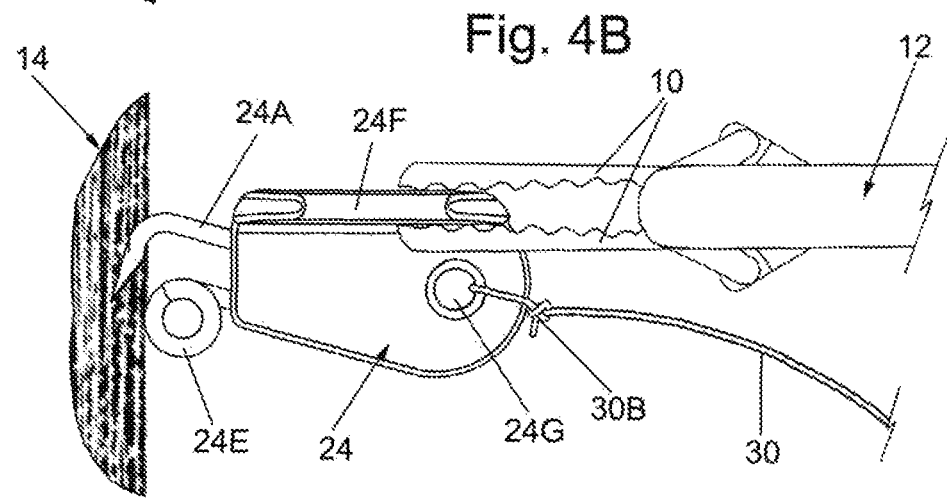

INTRA-ABDOMINAL LIVER RETRACTION DEVICE AND METHOD OF USE

CROSS-REFERENCE TO RELATED APPLICATIONS

This utility application claims the benefit under 35 U.S.C. § 119(e) of Provisional Application Ser. No. 62/820,368 filed on Mar. 19, 2019, entitled Intra-Abdominal Liver Retraction Device and Method of Use. The entire disclosure of the provisional application is incorporated by reference herein.

FIELD OF THE INVENTION

This invention relates generally to medical devices and methods of use and more particularly to devices and methods for lifting the liver or other organ in a patient during a laparoscopic procedure.

BACKGROUND OF THE INVENTION

During laparoscopic procedures in the abdomen an instrument, e.g., a grasper or retractor, may be used to lift or otherwise move an organ to a position so that it does not interfere with the laparoscopic procedure on another organ or anatomic structure/tissue (the "target") within the abdomen. The organ to be moved or lifted is susceptible to being scraped, punctured, bruised or otherwise damaged using the conventional retractors, clamps or graspers during laparoscopic surgical procedures to move it while the surgeon works on the target. This is particularly true of the liver. Thus some retractors include inflatable balloons and the like so to avoid unintentional damage to the organ being moved. However, such retractors are rather large and hence may block the field of view of the surgeon.

U.S. Pat. No. 8,449,461 (Kim et al.) discloses a surgical retractor capable of preventing an organ of a human body from being damaged when the organ of the human body positioned over a surgical area in the human body is lifted up. The surgical retractor includes a support body including a plurality of support members that are inserted below the organ to lift it upward. The plurality of support members are fastened to a joint, and a protective film member joined to the support body to cover a region between the support members, and configured to enclose and protect a lower surface of the organ.

U.S. Pat. No. 9,974,532 (Baas et al.) discloses a clip for organ retraction during minimally invasive surgery. The clip comprises a body made of a biocompatible material. The body comprises at least two generally opposing first and second segments that form a jaw defined by a separation between the two segments. The two segments each comprise distal and proximal ends wherein the proximal ends may be directly connected or connected through one or more segments within the body of the clip and wherein the clip defines at least four configurations a resting configuration, an open configuration, a grabbing configuration, and a sliding configuration. One embodiment is in the form of a system comprising a plurality of clips wherein each clip is attached to a band and wherein the bands can attach to each other to form a net for moving an organ or tissue.

United States Published Application 2009/0221868613 (Evans) discloses a sling anchor system for implanting support members in patients. The system includes a support member, such as a sling for urinary incontinence, tissue anchors, filamentary elements for associating the support member with the anchors, and introducer needles for placing the anchors in a patient. The support members can also be configured for use in pelvic floor repair, such as for treating cystoceles, rectoceles, and enteroceles.

United States Published Application 2018/0263613 (Wik et al.) discloses an organ retraction device for use during laparoscopic surgery. The device is in the form of a triangular fabric sling which is reinforced about its periphery. The sling has a curved needle connected to a first end of the sling by a first suture having one point of attachment to the sling and a straight needle connected to the second end of the sling by a second suture having two points of attachment on the sling. The sling is configured to support the liver of a patient in a "hammock" type structure during the procedure with the curved needle attached to the diaphragm of the patient and with the straight needle placed through the abdominal wall.

The patent literature includes disclosures of other sling or similar devices for use in the body of a patient for supporting tissue therein, such as: US2008/0081945 (Toso et al.); US2009/0137877 (Minnelli et al.); and US2009/0171143 (Chu et al.).

In a paper entitled "Newly Developed Liver-Retraction Method For Laparoscopic Gastric Surgery Using A Silicone Disc: The φ-Shaped Technique", by Hiroshi Saeki, MD, et al. appearing on pages e43-e46 of Journal Of American College Of Surgeons ©2013, there is disclosed a leaf shaped silicone disc having a flexible shape-memory frame for lifting the lateral segment of the liver of a patient. In particular, the procedure disclosed entails: (a) creating a small loop at the distal end of a 2-0 monofilament suture; (b) lifting up the lateral segment of the liver with forceps, and suturing one of the diaphragmatic crura; (c) cutting the suture needle extracorporeally; (d) passing the proximal end of the suture through the loop; (e) introducing the loop into the abdominal cavity and fixing it at the crus of the diaphragm; (f) passing the proximal end of the suture through two holes of the silicone disc, extracorporeally, across the desired disc axis; (g) introducing the silicone disc into the abdominal cavity and placing it under the liver, with the suture side down, (h) pulling the suture through the epigastrium; and (i) applying traction to the suture to allow the silicone disc to lift the lateral segment of the liver.

While the above identified prior art appears generally suitable for their intended purposes, they nevertheless leave something to be desired from one or more various structural and/or operational standpoints.

Thus, a need exists for a device which can be used during laparoscopic surgery to support a body organ, such as the liver, without injuring it, yet which is simple in construction, low in cost, easy to use, effective, and does not appreciably decrease the area of the surgical site and the field of view of the surgeon. The subject invention addresses that need.

BRIEF SUMMARY OF THE INVENTION

One aspect of this invention is an intra-abdominal liver retraction device for use in a patient having a liver, an abdomen, an abdominal wall and a diaphragm. The intra-abdominal liver retraction device comprises a sling, an anchor and a first flexible filament. The sling is formed of a flexible material and has a base edge, a pair of side edges tapering together from the base edge toward a leading edge. The sling includes a stiffening member extending across the sling between the side edges adjacent the base edge to enable the sling to be furled or otherwise gathered into a compact state adjacent the stiffening member so that the sling can be introduced through a small port into the abdomen, whereupon the sling can be opened into an un-gathered state. The anchor is flexibly connected to the base edge and configured be manipulated to pierce into and be releasably secured to the diaphragm from within the abdomen, whereupon the base edge is adjacent the diaphragm when the sling is in the un-gathered state to receive the liver thereon. The first flexible filament is connected to the panel adjacent the leading edge. The first flexible filament is configured to drawn from within the abdomen through an aperture in the abdominal wall to lift the sling with the liver thereon upward towards the abdominal wall.

In accordance with one preferred aspect of the intra-abdominal liver retraction device of this invention, the sling includes at least one tab or projection extending outward from each of the side edges. Each of the at least one tab is configured to be grasped by an intra-abdominal grasping tool to manipulate the sling to a desired position under the liver.

In accordance with another preferred aspect of the intra-abdominal liver retraction device of this invention, each of the at least one tab includes a hole therein to facilitate grasping of the at least one tab by the intra-abdominal grasping tool.

In accordance with another preferred aspect of the intra-abdominal liver retraction device of this invention, the sling is formed of a sheet of a flexible material. The sheet includes a portion that is folded over itself to form a fold at the base edge. The stiffening member comprises an elongated rod or strip of a rigid material disposed within the fold.

In accordance with another preferred aspect of the intra-abdominal liver retraction device of this invention, the sling is formed of a translucent material and includes plural lines extending across the sling between the side edges for enhancing visualization of the sling.

In accordance with another preferred aspect of the intra-abdominal liver retraction device of this invention, the anchor comprises a hook member and a graspable body from which a portion of the hook member extends.

In accordance with another preferred aspect of the intra-abdominal liver retraction device of this invention, the hook member comprises a piercing point and a rounded tissue engaging portion spaced slightly proximally from the piercing point.

In accordance with another preferred aspect of the intra-abdominal liver retraction device of this invention, the anchor is flexibly connected to the base edge by a second flexible filament.

Another aspect of this invention is a method of lifting the liver of a patient having an abdomen, an abdominal wall and a diaphragm. The method comprises providing an intra-abdominal liver retraction device comprising a sling, an anchor and a flexible filament. The sling is formed of a flexible material having a base edge and a stiffening member extending along the base edge. The sling is furled or otherwise gathered adjacent the stiffening member to cause it to be in a compact state. The intra-abdominal liver retraction device with the sling in the compact state is introduced through a small port in the abdominal wall into the abdomen. The sling is opened within the abdomen from the compact state to an un-gathered state. The anchor is releasably secured to the diaphragm so that a portion of the sling is releasably secured to the diaphragm with the base edge being adjacent the diaphragm. The sling is manipulated so that the liver is disposed on top of the sling. The flexible filament is drawn through an aperture in the abdominal wall from inside the abdomen to lift the sling with the liver thereon upward towards the abdominal wall.

In accordance with one preferred aspect of the method of this invention, the intra-abdominal liver retraction device with the sling in the compact state is introduced through the small port into the abdomen by use of a trocar extending through the small port.

In accordance with another preferred aspect of the method of this invention, the method additionally comprises piercing the abdominal wall from outside thereof to form the aperture. A grasping instrument is introduced through the aperture into the abdomen to grasp the first portion of the flexible filament. The first portion of the filament is drawn through the aperture to a position outside the abdominal wall.

In accordance with another preferred aspect of the method of this invention, the manipulating of the sling is accomplished by use of a grasping tool introduced through the abdominal wall.

In accordance with another preferred aspect of the method of this invention, the method additionally comprises releasing the anchor from the diaphragm of the patient by use of a grasping tool introduced through the abdominal wall.

In accordance with another preferred aspect of the method of this invention, the method additionally comprises introducing a trocar through the abdominal wall from outside the abdominal wall and grasping the intra-abdominal liver retraction device by a grasping tool inserted through the trocar and a pulling the intra-abdominal liver retraction device out of the abdomen through the trocar.

BRIEF DESCRIPTION OF THE DRAWING FIGURES

FIG. 2A is a slightly enlarged plan view of the sling component of the exemplary intra-abdominal liver retraction device shown in FIG. 1;

FIG. 2B is a side elevation view of the sling component shown in FIG. 2;

FIG. 3A is an enlarged side elevation view of the anchor component of the exemplary intra-abdominal liver retraction device shown in FIG. 1;

FIG. 3B is a top plan view of the anchor component shown in FIG. 3A;

FIG. 3C is an isometric view of one of the sections making up a portion of the anchor component shown in FIG. 3A;

FIG. 3D is a front elevation view of the anchor component shown in FIG. 3A;

FIG. 3E is an enlarged isometric view, partially in section, of the anchor component shown in FIG. 3A;

FIG. 4A is an illustration showing one step in the use of the exemplary intra-abdominal liver retraction device of this invention in accordance with a method of this invention; and FIG. 4B is an illustration, like FIG. 4A, but showing a subsequent step in the use of the exemplary intra-abdominal liver retraction device of this invention in accordance with a method of this invention.

DETAILED DESCRIPTION OF THE PREFERRED EMBODIMENTS OF THE INVENTION

Figure 1:
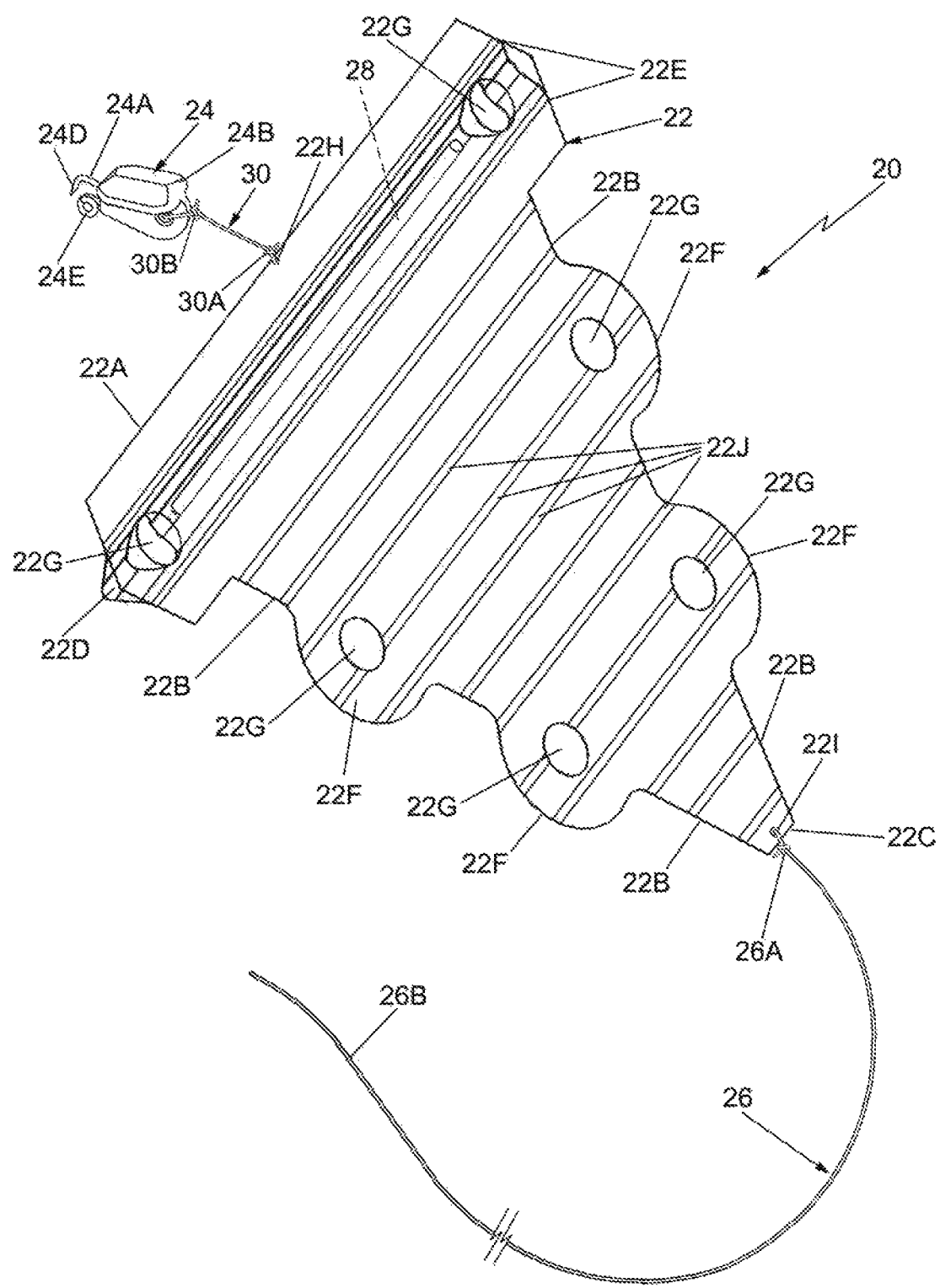
FIG. 1 is an isometric view of one exemplary intra-abdominal liver retraction device constructed in accordance with this invention.

Referring now to the various figures of the drawing wherein like reference characters refer to like parts, there is shown in FIG. 1 an exemplary intra-abdominal liver retraction device 20 constructed in accordance with this invention. As will be described in detail later, the device 20 is configured to be furled or otherwise collapsed so that it can be readily introduced through a conventional trocar or some other access port instrument into the abdominal cavity of a patient, and thereafter unfurled or otherwise opened so that the patient's liver can be disposed on the sling for lifting or otherwise retracting to provide access to some other anatomical structure in the abdominal cavity.

The intra-abdominal liver retraction device 20 basically comprises a support panel or sling 22, an anchor 24, and an elevating or lifting filament 26. The sling is formed of a sheet or web of a flexible material, e.g., polyurethane. The sheet or web is sufficiently thin, e.g., approximately 6 mil, in the interest of flexibility, but still sufficiently thick and strong to be able to safely support and lift the liver of an adult thereon. The sling is in the form of wedge or triangularly shaped member having a base edge 22A, a pair of side edges 22B tapering together from the base edge toward a leading edge 22C. The base edge is linear, but may be arcuate. The leading edge 22C may be in the form of a point or a short linear or arcuate edge which is significantly shorter in length than the base edge 22A. The portion of the sheet or web making up the sling is of double thickness adjacent the base edge to form a channel 22D extending along the base edge between the side edges 22B. The channel serves to hold a thin, elongated stiffening rod 28 therein. The stiffening rod is formed of any suitable light-weight yet strong material, e.g., Nylon. If desired, the rod may be replaced with a flat strip. In the exemplary embodiment shown the double thickness portion of the sling forming the channel 22D is created by folding the portion of the sheet making up the sling over on itself, and sealing the free edge thereof along a transverse heat seal line 22E to form the channel 22D. Thus, the fold line of the channel forms the base edge 22A of the sling to complete the channel 22D. Another transverse heat seal line 22E is provided between the stiffening rod and the fold forming the base edge 22A. The stiffening rod 28 is held within the channel 22D by respective heat seals (not shown) at the respective ends of the channel. The stiffening rod can be held in place by other means, e.g., an adhesive, etc.

A plurality of tabs 22F project outward from the side edges 22B of the sling. As will be described later, each tab serves as a convenient location or point on the sling to be grasped by a conventional laparoscopic grasper or other grasping instrument within the abdominal cavity in order to manipulate the sling to facilitate its introduction into the abdominal cavity via the trocar or some other access port device, to unfurl or otherwise open the sling from the compact condition or state that it is in when it passes through the trocar, and to move the sling to the proper orientation and position for use. In order to enhance the grasp-ability of the sling each of the tabs 22F includes a hole or opening 22G for receipt of the jaws of a conventional laparoscopic grasper or any other suitable grasping instrument used to manipulate and orient the sling.

In the exemplary embodiment shown the sling is of generally wedge or triangular shape and has a maximum width of approximately 4 inches and a maximum length of approximately 3 inches. Those dimensions are merely exemplary and the sling can be of other sizes and shapes so long as its side edges taper together from its base edge towards its leading edge. Moreover, the base edge and the leading edge need not be linear as shown.

The details of the construction and operation of the anchor 24 will be described later. Suffice it for now to state that the anchor is connected to the sling at the middle of the base edge by means of a short length, e.g., approximately 0.75 in, of a flexible filament 30. The filament 30 can be formed of any suitable material, e.g., conventional surgical suture material, and can be a monofilament member or a multifilament member. One end of the filament 30 is extended through a small aperture 22H (FIG. 2) in the sling adjacent the base edge 22A and is secured thereto by a knot 30A. The opposite end of the filament 30 is connected to the anchor 24 by means of a knot 30B. With the anchor 24 attached to the sling 22 as just described, the anchor can be readily grasped and manipulated to be releasably secured to the diaphragm, whereupon the base edge 22A of the sling is adjacent the diaphragm.

The elevating or lifting filament 26 is formed of any suitable material, e.g., the same material forming the filament 30, but is significantly longer in length, e.g., approximately 8.0 inches. One end of the filament 26 is extended through a small aperture 22I (FIG. 2) in the sling adjacent the leading edge 22C and is secured thereto by a knot 26A. The opposite end portion 26B of the filament is free and is configured to be carried from inside the abdominal cavity through a small aperture in the abdominal wall to a position outside the abdominal wall as will be described later.

In the interest of facilitating the visibility of structures within the abdominal cavity, the sling 22 is preferably translucent to enable light to shine therethrough, so that the sling will not obscure or otherwise interfere with the field of view of the surgeon performing the laparoscopic procedure. However, being translucent, it is desirable that a portion of the sling be readily visually discernable to facilitate the manipulation, placement and orientation of the sling. To that end the sling includes plural visually discernable lines 22J extending across the width of the sling between its side edges 22B from the base edge to the leading edge. The lines 22J can be formed by heat sealing bars. Alternatively, the lines 22J can be formed by other means. For example they can be printed on the sling or otherwise applied to the sling. Moreover, the lines need not be continuous lines, but may be broken. In fact, other visually perceptible markings can be used in place of the lines 22J to facilitate visualization of the sling during use of the intra-abdominal liver retraction device 20.

Turning now to FIGS. 3A-3E the details of the anchor 24 will now be described. As can be seen the anchor basically comprises a hook member 24A and a graspable body member referred to as a "grip block" 24B. The grip block 24B holds the hook member 24A and is formed of two mirrored sections 24B' (one of which is shown in FIG. 3C) and which are joined together. The sections 24B' are formed of any suitable material, e.g., Acrylonitrile Butadiene Styrene (ABS), and joined together by any suitable means, e.g., an ultraviolet (UV)-activated adhesive. The sections 24B' each includes a generally U-shaped channel 24C (FIG. 3C), which conjoin when the two sections 24B' are joined together, to hold a corresponding portion of the hook member 24A therein. The grip block 24 serves as the means for grasping and orienting the anchor during usage of the intra-abdominal liver retraction device 20, as will be described later.

The hook member 24A is best seen in FIGS. 3A, 3B, 3D and 3E and basically comprises a generally U-shaped member having a pair of parallel legs. One of the legs of the U-shaped member terminates in a piercing point 24D which extends perpendicularly to the leg from which it extends.

The other of the legs of the U-shaped member terminates in a corkscrew shaped guard portion 24E located slightly proximally of the piercing point 24D. The piercing point 24D is sharpened at its free end so that it can readily pierce and be releasably retained within the diaphragm of the patient when the intra-abdominal liver retraction device 20 is used. The guard portion 24E serves as a protective feature. In particular, in the event that the anchor 24 is dropped during its placement, the rounded bottom surface of the guard portion 24E will engage any tissue located below the anchor before the sharp point engages that tissue, thereby protecting that underlying tissue from injury by the sharp point. Moreover, the guard portion 24E is configured to engage the surface of the diaphragm when the anchor is properly oriented to releasably secure it to the diaphragm. The hook member 24 can be formed of any material, e.g., surgical steel, suitable for readily piercing and being releasably secured to the diaphragm of the patient.

As mentioned above, the grip block 24B serves as the means for grasping and manipulating the anchor 24 by a grasper or other grasping device. To that end, each of the sections 24B' includes an outwardly extending flange or wing 24F contiguous with the top surface of the section. As best seen in FIGS. 4A and 4B, each wing 24F is shaped and sized to be readily grasped by the jaws 10 of a conventional laparoscopic grasper 12 or any other suitable laparoscopic grasping instrument to facilitate the releasable securement of the anchor to the patient's diaphragm 24. The grip block 24B also includes an opening or hole 24G formed by conjoining holes 24G' in the grip block sections 24B'. The hole 24G serves to receive the knotted end 30B of the filament 30 to secure the anchor to the sling 22.

The length of the exemplary anchor 24 shown is approximately 0.75 inch, with the length of the grip block 24B being approximately 0.5 inch, and with the length of the hook member 24A being approximately 0.5 inch and extending out of the distal end of the grip block by approximately 0.25 inch. Moreover, the gap 24H (FIG. 3E) between the piercing point 24D and the corkscrew portion 24E is approximately 0.1 inch. Those dimensions are merely exemplary, and the anchor and its components can be either somewhat larger or somewhat smaller.

Attention is now directed at FIGS. 4A and 4B where the use of the intra-abdominal liver retraction device 20 using the method of this invention will now be described. In particular, a conventional trocar or some other access port is introduced into the patient's abdominal cavity where the laparoscopic procedure is to be carried out. The device 20 is furled or otherwise gathered adjacent its base edge so that it is in a compact state suitable for introduction through the trocar into the abdominal cavity. The fact that the stiffening rod is confined to the base edge while the remaining portions of the sling 22 are flexible facilitates the furling or otherwise gathering of the sling to the compact state for insertion through the trocar. A grasping instrument, like instrument 12 shown in FIGS. 4A and 4B or any other suitable laparoscopic grasping instrument, can be used within the abdominal cavity to push the device 20 through the trocar and into the abdominal cavity, whereupon the sling can be unfurled or otherwise opened to a relatively flat state. Any of the tabs 22F and/or the holes 22G can serve as points on the sling which can be readily grasped by the jaws 10 of the grasper 12 to facilitate the unfurling of the sling into the aforementioned flat state within the abdominal cavity.

one of the wings 24F of the anchor 24 can then be grasped by the jaws 10 of the grasper 12 to move the anchor to a position such that the piercing tip 24D is confronting the patient's diaphragm 14 like shown in FIG. 4A. In that orientation and position the wings 24F of the anchor will be generally horizontal and the piercing tip 24D will extend at an acute angle to the surface of the diaphragm. The grasper 12 can then be moved to cause the piercing tip to pierce into the diaphragm like shown in FIG. 4B. This action releasably secures the anchor 24 to the diaphragm, with the base edge 22A of the sling 22 closely adjacent, e.g., approximately 1.50 inch, from the diaphragm. In that state the sling is stable and can be readily manipulated by the surgeon using the jaws of another grasper to grasp any of the sling's tabs 22F/holes 22G so that the sling is located under the patient's liver.

After the sling 22 has been releasably secured to the diaphragm 14 and located under the patient's liver a conventional needle-driver or some other piercing instrument can be used to pierce the abdominal wall from the outside to create a first or exit aperture in the abdominal wall. It is through that exit aperture that the free end portion 26B of the lifting filament 26 will be drawn from inside the abdominal cavity to a position outside the abdominal cavity. If the needle which makes the exit aperture in the abdominal wall includes some type of grasping feature it can be used to grasp the free end portion 26B and carry it from inside the abdominal cavity to outside the abdominal cavity. If that needle doesn't include any such grasping feature another instrument having a grasping feature can be introduced through the exit aperture into the abdominal cavity to grasp the free end portion 26B of the filament and carry it out through the exit aperture to outside the abdominal wall. In any case the free end portion 26B of the lifting filament 26 is pulled upward eternally until the desired lift is achieved and then held in place at this height with a common surgical clamp such as a hemostat. That action will lift, elevate or otherwise retract the liver to a desired elevated position adjacent the abdominal wall, thereby providing the surgeon with room to perform the laparoscopic procedure without interference from the liver.

Once the laparoscopic procedure has been completed and it is desired to relocate the liver to its normal position, all that is required is to use the jaws 10 of a grasper 12 to grasp one of the wings 24B' of the anchor so that the anchor can be manipulated to a position wherein the sharp point 24C of the hook 24A is released from the diaphragm. Once the anchor is free of the diaphragm and the external clamp is removed, a grasper 12 or some other grasping instrument can be used to grasp a portion of the lifting filament 26 that is between the sling and the exit aperture to pull or apply traction to that filament portion. That action draws the free end 26B of the filament 26 back through the exit aperture so that the entire filament will be within the abdominal cavity. At that point the intra-abdominal liver retraction device 20 is ready to be removed from the abdominal cavity.

The device removal action is achieved by inserting a trocar into the abdominal cavity. A grasping instrument 12 can then be used to grasp and manipulate the sling 22 so that it is furled or otherwise gathered and then introduced into the trocar. Once a portion of the device 20 is within the trocar it can be grasped by another grasping instrument extended into the trocar from outside the patient so that the device 20 can be pulled out of the body of the patient through the trocar.

It should be appreciated by those skilled in the art, that while the intra-abdominal liver retraction device 20 of the subject invention has particular utility for retracting the liver of a patient, the device is not limited to use with that particular organ. Thus, devices constructed in accordance with this invention and their method of used can be used to elevate or retract other organs or anatomic structures within the body of a patient during a laparoscopic procedure. Further still, various changes can be made to the structure of the device and its methods of use, other than those specifically described or disclosed above.

Without further elaboration the foregoing will so fully illustrate our invention that others may, by applying current or future knowledge, adopt the same for use under various conditions of service.

We claim:

1. An intra-abdominal liver retraction device for use in a patient, the patient having a liver, an abdomen, an abdominal wall and a diaphragm, said intra-abdominal liver retraction device comprising:
    a sling formed of a flexible material and having a base edge, a pair of side edges tapering together from said base edge toward a leading edge, said sling including a stiffening member extending across said sling between said side edges adjacent said base edge to enable said sling to be furled or otherwise gathered into a compact state adjacent said stiffening member so that said sling can be introduced through a small port into the abdomen, whereupon said sling can be opened into an un-gathered state;
    an anchor flexibly connected to said base edge and configured be manipulated to pierce into and be releasably secured to the diaphragm from within the abdomen, whereupon said base edge is adjacent the diaphragm when said sling is in said un-gathered state to receive the liver thereon; and
    a first flexible filament connected to said sling adjacent said leading edge, said first flexible filament being configured to be drawn from within the abdomen through an aperture in the abdominal wall to lift said sling with the liver thereon upward towards the abdominal wall.

2. The intra-abdominal liver retraction device of claim 1, wherein said sling includes at least one tab or projection extending outward from each of said side edges, each of said at least one tabs being configured to be grasped by an intra-abdominal grasping tool to manipulate said sling to a desired position under the liver.

3. The intra-abdominal liver retraction device of claim 2, wherein each of said at least one tab includes a hole therein to facilitate grasping of said at least one tab by the intra-abdominal grasping tool.

4. The intra-abdominal liver retraction device of claim 1, wherein said sling includes a stiffening member extending across said sling between said side edges and adjacent said base edge.

5. The intra-abdominal liver retraction device of claim 4, wherein said sling is formed of a sheet of a flexible material, said sheet including a portion that is folded over itself to form a fold at said base edge, said stiffening member comprising an elongated rod or strip of a rigid material disposed within said fold.

6. The intra-abdominal liver retraction device of claim 1, wherein said sling is formed of a translucent material and includes plural lines extending across said sling between said side edges for enhancing visualization of said sling.

7. The intra-abdominal liver retraction device of claim 1, wherein said anchor comprises a hook member and a graspable body from which a portion of said hook member extends.

8. The intra-abdominal liver retraction device of claim 7, wherein said hook member comprises a piercing point and a rounded guard portion spaced slightly proximally of the piercing point.

9. The intra-abdominal liver retraction device of claim 1, wherein said anchor is flexibly connected to said base edge by a second flexible filament.

10. A method of lifting the liver of a patient, the patient having an abdomen, an abdominal wall and a diaphragm, said method comprising:
    providing an intra-abdominal liver retraction device comprising a sling, an anchor and a flexible filament, said sling being formed of a flexible material having a base edge and a stiffening member extending along the base edge;
    furling or otherwise gathering said sling adjacent said stiffening member to cause it to be in a compact state;
    introducing said intra-abdominal liver retraction device with said sling in said compact state through a small port in the abdominal wall into the abdomen;
    opening said sling within the abdomen from said compact state to an un-gathered state;
    releasably securing said anchor to the diaphragm so that a portion said sling is releasably secured to the diaphragm with said base edge being adjacent the diaphragm;
    manipulating said sling so that the liver is disposed on top of said sling; and
    drawing said flexible filament through an aperture in the abdominal wall from outside the abdomen to lift said sling with the liver thereon upward towards the abdominal wall.

11. The method of claim 10, wherein said intra-abdominal liver retraction device with said sling in said compact state is introduced through said small port into the abdomen by use of a trocar extending through said small port.

12. The method of claim 11, additionally comprising:
    piercing the abdominal wall from outside thereof to form said aperture;
    introducing a grasping instrument through said aperture into the abdomen to grasp a first portion of said flexible filament; and
    drawing said first portion of said filament through said aperture to a position outside the abdominal wall.

13. The method of claim 12, additionally comprising:
    releasing said anchor from the diaphragm of the patient by use of a grasping tool introduced through the abdominal wall;
    introducing a trocar through the abdominal wall from outside the abdominal wall; and
    grasping said intra-abdominal liver retraction device by a grasping tool inserted through said trocar and pulling said intra-abdominal liver retraction device out of the abdomen through said trocar.

14. The method of claim 11, additionally comprising:
    releasing said anchor from the diaphragm of the patient by use of a grasping tool introduced through the abdominal wall;
    introducing a trocar through the abdominal wall from outside the abdominal wall; and
    grasping said intra-abdominal liver retraction device by a grasping tool inserted through said trocar and pulling said intra-abdominal liver retraction device out of the abdomen through said trocar.

15. The method of claim 10, additionally comprising:
    piercing the abdominal wall from outside thereof to form said aperture;

introducing a grasping instrument through said aperture into the abdomen to grasp a first portion of said flexible filament; and drawing said first portion of said filament through said aperture to a position outside the abdominal wall.

16. The method of claim 15, wherein said manipulating of said sling is accomplished by use of a grasping tool introduced through the abdominal wall.

17. The method of claim 15, additionally comprising releasing said anchor from the diaphragm of the patient by use of a grasping tool introduced through the abdominal wall.

18. The method of claim 10, wherein said manipulating of said sling is accomplished by use of a grasping tool introduced through the abdominal wall.

19. The method of claim 10, additionally comprising releasing said anchor from the diaphragm of the patient by use of a grasping tool introduced through the abdominal wall.

20. The method of claim 10, additionally comprising:
  releasing said anchor from the diaphragm of the patient by use of a grasping tool introduced through the abdominal wall;
  introducing a trocar through the abdominal wall from outside the abdominal wall; and
  grasping said intra-abdominal liver retraction device by a grasping tool inserted through said trocar and pulling said intra-abdominal liver retraction device out of the abdomen through said trocar.

\* \* \* \* \*